(12) United States Patent
Jenney et al.

(10) Patent No.: US 12,350,489 B2
(45) Date of Patent: Jul. 8, 2025

(54) ELECTRODE LEADS HAVING NERVE CUFFS AND ASSOCIATED SYSTEMS AND METHODS

(71) Applicant: The Alfred E. Mann Foundation for Scientific Research, Valencia, CA (US)

(72) Inventors: Christopher Reed Jenney, Valencia, CA (US); Oren Gotlib, Agoura Hills, CA (US); Joseph Calderon, Santa Clarita, CA (US); William Andrew Brandt, Castaic, CA (US); Neil Talbot, La Crescenta, CA (US)

(73) Assignee: The Alfred E. Mann Foundation for Scientific Research, Valencia, CA (US)

( * ) Notice: Subject to any disclaimer, the term of this patent is extended or adjusted under 35 U.S.C. 154(b) by 445 days.

(21) Appl. No.: 17/683,598

(22) Filed: Mar. 1, 2022

(65) Prior Publication Data
US 2022/0313987 A1   Oct. 6, 2022

Related U.S. Application Data

(60) Provisional application No. 63/167,756, filed on Mar. 30, 2021.

(51) Int. Cl.
*A61N 1/05* (2006.01)
*A61N 1/36* (2006.01)
(Continued)

(52) U.S. Cl.
CPC ......... *A61N 1/0556* (2013.01); *A61N 1/3752* (2013.01); *H01R 13/5224* (2013.01); *A61N 2001/0578* (2013.01); *H01R 2201/12* (2013.01)

(58) Field of Classification Search
CPC ................ A61N 1/0556; A61N 1/3752; A61N 2001/0578; A61N 1/0558; A61N 1/3605;
(Continued)

(56) References Cited

U.S. PATENT DOCUMENTS 4,573,481 A   3/1986 Bullara
4,602,624 A   7/1986 Naples et al.
(Continued)

FOREIGN PATENT DOCUMENTS

WO   WO 2008092246 A1   8/2008
WO   WO 2009045772 A1   4/2009
(Continued)

OTHER PUBLICATIONS

PCT International Search and Written Opinion dated Jun. 17, 2022 for PCT App. Ser. No. PCT/US2022/018263.
(Continued)

*Primary Examiner* — Carl H Layno
*Assistant Examiner* — Anh-Khoa N Dinh
(74) *Attorney, Agent, or Firm* — Henricks Slavin LLP (57) ABSTRACT

An electrode that includes an elongate lead body and a nerve cuff. The nerve cuff may include a biologically compatible, elastic, electrically insulative cuff body configured to be circumferentially disposed around a nerve, first and second relatively wide electrically conductive contacts carried by the cuff body that are spaced from one another in the length direction and that extend in the width direction to such an extent that they extend completely around the cuff body inner lumen when the cuff body is in the pre-set furled shape, and a plurality of relatively narrow electrically conductive contacts carried by the cuff body that are spaced from one another in the width direction and are located between the first and second relatively wide electrically conductive contacts.

6 Claims, 9 Drawing Sheets

(51) Int. Cl.
   *A61N 1/375*   (2006.01)
   *H01R 13/52*   (2006.01)
(58) Field of Classification Search
   CPC .. A61N 1/375; A61N 1/0551; A61N 1/36139;
            A61N 1/05; A61N 7/00; A61N 5/00;
            A61N 7/022; A61N 1/3601; A61N
            1/36017; A61N 1/0534; A61N 1/3611;
            A61N 1/36185; A61N 1/36053; A61N
            1/36071; A61N 1/0456; A61N 1/36114;
            A61N 1/0531; A61N 1/0529; A61N
            1/37205; A61N 1/36171; A61N 1/36007;
            A61N 1/36146; A61N 1/36175; A61N
            1/0539; A61N 1/36117; A61N 1/0543;
            A61N 1/36021; H01R 13/5224; H01R
            2201/12
   See application file for complete search history.

(56) References Cited

U.S. PATENT DOCUMENTS

| | | | |
|---|---|---|---|
| 4,940,065 | A | 7/1990 | Tanagho et al. |
| 5,251,634 | A | 10/1993 | Weinberg |
| 5,400,784 | A | 3/1995 | Durand et al. |
| 5,439,485 | A | 8/1995 | Mar et al. |
| 5,487,756 | A | 1/1996 | Kallesoe et al. |
| 5,634,462 | A | 6/1997 | Tyler et al. |
| 5,919,220 | A | 7/1999 | Stieglitz et al. |
| 6,066,165 | A | 5/2000 | Racz |
| 6,210,339 | B1 | 4/2001 | Kiepen et al. |
| 6,292,703 | B1 | 9/2001 | Meier et al. |
| 7,383,090 | B2 | 6/2008 | O'Brien et al. |
| 7,794,256 | B1 | 9/2010 | Sochor |
| 7,809,442 | B2 | 10/2010 | Bolea et al. |
| 7,996,092 | B2 * | 8/2011 | Mrva ............... A61N 1/0556 607/118 |
| 8,116,882 | B2 | 2/2012 | Kowalczewski |
| 8,155,757 | B1 | 4/2012 | Neisz et al. |
| 8,224,449 | B2 | 7/2012 | Carbunaru et al. |
| 8,311,645 | B2 | 11/2012 | Bolea et al. |
| 8,340,785 | B2 | 12/2012 | Bonde et al. |
| 8,660,665 | B2 | 2/2014 | Walter et al. |
| 8,792,973 | B2 | 7/2014 | Moran et al. |
| 8,934,992 | B2 | 1/2015 | Johnson et al. |
| 9,186,511 | B2 | 11/2015 | Bolea |
| 9,227,053 | B2 | 1/2016 | Bonde et al. |
| 9,549,708 | B2 | 1/2017 | Mercanzini et al. |
| 9,603,538 | B2 | 3/2017 | Fisher et al. |
| 9,849,288 | B2 | 12/2017 | Meadows et al. |
| 9,889,304 | B2 | 2/2018 | Mercanzini |
| 9,931,045 | B2 | 4/2018 | Brunnett et al. |
| 10,758,723 | B2 | 9/2020 | Fang et al. |
| 11,833,348 | B2 | 12/2023 | Brandt et al. |
| 2002/0198582 | A1 | 12/2002 | Edell et al. |
| 2005/0070982 | A1 | 3/2005 | Heruth et al. |
| 2005/0186829 | A1 | 8/2005 | Balsells |
| 2006/0004430 | A1 | 1/2006 | Rossing et al. |
| 2006/0030919 | A1 | 2/2006 | Mrva et al. |
| 2007/0123765 | A1 | 5/2007 | Hetke et al. |
| 2007/0185542 | A1 | 8/2007 | Bolea et al. |
| 2008/0082137 | A1 | 4/2008 | Kieval et al. |
| 2008/0092246 | A1 | 4/2008 | Shintani |
| 2008/0103545 | A1 | 5/2008 | Bolea et al. |
| 2008/0172101 | A1 | 7/2008 | Bolea et al. |
| 2009/0045772 | A1 | 2/2009 | Cook et al. |
| 2009/0132042 | A1 | 5/2009 | Hetke et al. |
| 2009/0210042 | A1 | 8/2009 | Kowalczewski |
| 2010/0305674 | A1 | 12/2010 | Zarembo et al. |
| 2010/0331933 | A1 | 12/2010 | Carbunaru et al. |
| 2011/0066196 | A1 | 3/2011 | Alexander et al. |
| 2011/0130815 | A1 | 6/2011 | Gibson et al. |
| 2011/0154655 | A1 | 6/2011 | Hetke et al. |
| 2011/0251473 | A1 | 10/2011 | Moran et al. |
| 2011/0301665 | A1 | 12/2011 | Mercanzini et al. |
| 2012/0089153 | A1 | 4/2012 | Christopherson et al. |
| 2012/0150255 | A1 | 6/2012 | Lindenthaler et al. |
| 2012/0154256 | A1 | 6/2012 | Grover et al. |
| 2012/0277819 | A1 | 11/2012 | Cowley et al. |
| 2012/0316417 | A1 | 12/2012 | Vetter |
| 2013/0030352 | A1 | 1/2013 | Seymour et al. |
| 2013/0085361 | A1 | 4/2013 | Mercanzini et al. |
| 2013/0090711 | A1 | 4/2013 | Ramachandran et al. |
| 2013/0150938 | A1 | 6/2013 | Carbunaru et al. |
| 2013/0304174 | A1 | 11/2013 | Langhals et al. |
| 2014/0005763 | A1 | 1/2014 | Cederna et al. |
| 2014/0058482 | A1 | 2/2014 | Gupta et al. |
| 2014/0163659 | A1 | 6/2014 | Boling |
| 2014/0188202 | A1 | 7/2014 | Zarembo et al. |
| 2014/0228905 | A1 | 8/2014 | Bolea |
| 2014/0303703 | A1 | 10/2014 | Mercanzini et al. |
| 2015/0119673 | A1 | 4/2015 | Pellinen et al. |
| 2015/0128413 | A1 | 5/2015 | Vetter et al. |
| 2015/0157854 | A1 | 6/2015 | Hetke et al. |
| 2015/0174396 | A1 | 6/2015 | Fisher et al. |
| 2015/0224307 | A1 | 8/2015 | Bolea |
| 2015/0374975 | A1 | 12/2015 | Callegari et al. |
| 2016/0184581 | A1 | 6/2016 | Bonde et al. |
| 2016/0199637 | A1 | 7/2016 | Xu et al. |
| 2016/0287863 | A1 | 10/2016 | Mercanzini et al. |
| 2016/0331326 | A1 | 11/2016 | Xiang et al. |
| 2016/0331994 | A1 | 11/2016 | Smith et al. |
| 2017/0266436 | A1 | 9/2017 | Suwito et al. |
| 2017/0319846 | A1 | 11/2017 | Plachta et al. |
| 2018/0117313 | A1* | 5/2018 | Schmidt ............... A61N 1/3752 |
| 2018/0132790 | A1 | 5/2018 | Yao et al. |
| 2018/0221660 | A1 | 8/2018 | Suri et al. |
| 2018/0318577 | A1 | 11/2018 | Ng et al. |
| 2018/0318578 | A1 | 11/2018 | Ng et al. |
| 2019/0060646 | A1 | 2/2019 | Ng et al. |
| 2019/0069949 | A1 | 3/2019 | Vrba et al. |
| 2019/0282805 | A1 | 9/2019 | Schmidt et al. |
| 2020/0069935 | A1 | 3/2020 | Johnson et al. |
| 2020/0083922 | A1 | 3/2020 | Hong et al. |
| 2020/0146583 | A1 | 5/2020 | Hestad et al. |
| 2020/0230412 | A1 | 7/2020 | Rondoni et al. |
| 2020/0230421 | A1 | 7/2020 | Zaidi et al. |
| 2020/0306526 | A1 | 10/2020 | Doguet et al. |
| 2021/0205662 | A1 | 7/2021 | Lu et al. |
| 2022/0062629 | A1 | 3/2022 | Dearden |
| 2022/0088374 | A1 | 3/2022 | Ackermann et al. |
| 2023/0010510 | A1 | 1/2023 | Brandt et al. |
| 2023/0241394 | A1 | 8/2023 | Jenny et al. |
| 2024/0009452 | A1 | 1/2024 | Jenny et al. |
| 2024/0058602 | A1 | 2/2024 | Brandt et al. |
| 2024/0108883 | A1 | 4/2024 | Trivedi et al. |

FOREIGN PATENT DOCUMENTS

| | | |
|---|---|---|
| WO | WO 2012154256 A1 | 11/2012 |
| WO | WO 2013188871 A1 | 12/2013 |
| WO | WO 2016039768 A1 | 3/2016 |
| WO | WO 2020182293 A1 | 9/2020 |
| WO | WO 2021108810 A1 | 6/2021 |

OTHER PUBLICATIONS

U.S. Appl. No. 17/463,611 filed Sep. 1, 2021.
U.S. Appl. No. 17/463,630 filed Sep. 1, 2021.
U.S. Appl. No. 18/495,503 filed Oct. 26, 2023.
U.S. Appl. No. 17/683,598 filed Mar. 1, 2022.
U.S. Appl. No. 17/710,570 filed Mar. 31, 2022.
U.S. Appl. No. 18/468,730 filed Sep. 17, 2023.
U.S. Appl. No. 18/186,927 filed Mar. 20, 2023.

* cited by examiner

ELECTRODE LEADS HAVING NERVE CUFFS AND ASSOCIATED SYSTEMS AND METHODS

CROSS-REFERENCE TO RELATED APPLICATION

This application claims the benefit of U.S. Provisional Application No. 63/167,756, filed Mar. 30, 2021, and entitled "Hypoglossal Nerve Cuff Electrode Design," which is incorporated herein by reference.

BACKGROUND OF THE INVENTIONS

1. Field of Inventions

The present inventions relate generally to the treatment of obstructive sleep apnea by stimulating the hypoglossal nerve.

2. Description of the Related Art

Obstructive sleep apnea (OSA) is a highly prevalent sleep disorder that is caused by the collapse of or increase in the resistance of the pharyngeal airway, often resulting from tongue obstruction. The obstruction of the upper airway is mainly caused by reduced genioglossus muscle activity during the deeper states of non-rapid eye movement (NREM) sleep. In some OSA patients, obstruction occurs predominantly during rapid eye movement (REM) sleep. This is known as REM OSA and has different cardiometabolic and neurocognitive risks. Obstruction of the upper airway causes breathing to pause during sleep. Cessation of breathing, in turn, causes a decrease in the blood oxygen saturation level, which is eventually corrected when the person wakes up and resumes breathing. The long-term effects of OSA include, but are not limited to, high blood pressure, heart failure, strokes, diabetes, headaches, and general daytime sleepiness and memory loss.

Some proposed methods of alleviating apneic events involve the use of neurostimulators to open the upper airway. Such therapy involves stimulating the nerve fascicles of the hypoglossal nerve (HGN) that innervate the intrinsic and extrinsic muscles of the tongue in a manner that prevents retraction of the tongue, which would otherwise close the upper airway during the inspiration portion of the respiratory cycle. In some instances, the trunk of the HGN is stimulated with a nerve cuff, including a cuff body and a plurality of electrically conductive contacts on the cuff body, that is positioned around the HGN trunk. The HGN trunk nerve cuff may be configured in such a manner that it can be used to selectively stimulate nerve fascicles which innervate muscles that extend the tongue, while avoiding other nerve fascicles, with what is predominantly radial vector stimulation. For example, the contacts may be axially aligned and circumferentially spaced around the perimeter of the HGN trunk. In other instances, a nerve cuff is placed on the branch of the HGN that is responsible for protruding the tongue (hereafter "HGN genioglossus muscle branch" or "HGN GM branch"). A smaller diameter cuff with two or three axially spaced contacts may be used at the HGN GM branch because the nerve fascicles within this branch generally innervate the specific tongue protrusor muscle, but not other muscles. Put another way, the entire HGN GM branch is stimulated with what is predominantly axial vector stimulation. Exemplary nerve cuffs are illustrated and described in U.S. Pat. Pub. Nos. 2018/0318577A1, 2018/0318578A1, 2019/0060646A1 and 2019/0282805, which are incorporated herein by reference in their entirety.

SUMMARY

The present inventors have determined that nerve cuffs are susceptible to improvement. In particular, at least some nerve cuffs include electrically conductive members that are laminated between two non-conductive layers, with one of the conductive layers including openings that expose the conductive members. The present inventors have determined that certain electrically conductive materials with otherwise desirable properties (e.g., platinum-iridium) do not bond well with the adhesive (e.g., silicone adhesive) that is used to bond non-conductive layers that are formed from materials that have desirable mechanical properties (e.g., silicone). The less than optimal bond may lead to delamination of the nerve cuff, and the present inventors have determined that it would be desirable to provide nerve cuffs that, among other things, employ materials and adhesives with desired properties in a manner that reduces the likelihood of delamination. The present inventors have further determine that it would be desirable to provide nerve cuffs with conductive member arrangements that improve the flexibility of the nerve cuffs.

An electrode lead in accordance with at least one of the present inventions includes an elongate lead body and a nerve cuff. The nerve cuff may include a cuff body affixed to the distal end of the lead body, first and second relatively wide electrically conductive members located between the first and second layers of the cuff body, spaced from one another in the length direction, and extending in the width direction to such an extent that they extend completely around the cuff body inner lumen when the cuff body is in the pre-set furled shape, the cuff body front layer including a plurality of openings that are spaced from one another in the width direction and are aligned with, and located inwardly of the perimeter of, the first relatively wide electrically conductive member and a plurality of openings that are spaced from one another in the width direction and are aligned with, and located inwardly of the perimeter of, the second relatively wide electrically conductive member, a plurality of relatively narrow electrically conductive members located between the first and second layers of the cuff body, the cuff body front layer including a plurality of openings that are spaced from one another in the width direction and are respectively aligned with the relatively narrow electrically conductive members, and a plurality of electrical conductors extending through the lead body from at least some of the electrically conductive contacts to the proximal end of the lead body.

An electrode lead in accordance with at least one of the present inventions includes an elongate lead body and a nerve cuff. The nerve cuff may include a cuff body affixed to the distal end of the lead body, a first row of electrically conductive contacts carried by the cuff body that are spaced from one another in the width direction and are connected to one another in series by flexible conductors that extend in the length direction, a second row of electrically conductive contacts carried by the cuff body that are spaced from one another in the width direction, the second row being spaced from the first row in the length direction, a third row of electrically conductive contacts carried by the cuff body that are spaced from one another in the width direction, the third row being located between the first and second rows, and a plurality of electrical conductors extending through the lead body from at least some of the electrically conductive contacts to the proximal end of the lead body.

An electrode lead in accordance with at least one of the present inventions includes an elongate lead body and a nerve cuff. The nerve cuff may include a first row of electrically conductive members carried by the cuff body, spaced from one another in the width direction, and defining first and second longitudinal ends and a length that is perpendicular to the width direction, at least some of the electrically conductive members in the first row being connected to one another in series by at least one conductor that is connected to one of the longitudinal ends of the connected electrically conductive members by a joint and that extends in the width direction, a second row of electrically conductive members carried by the cuff body, spaced from one another in the width direction, the second row being spaced from the first row in the length direction, a third row of electrically conductive members carried by the cuff body that are spaced from one another in the width direction, the third row being located between the first and second rows, and a plurality of electrical conductors extending through the lead body from at least some of the electrically conductive members to the proximal end of the lead body.

An electrode lead in accordance with at least one of the present inventions includes an elongate lead body and a nerve cuff. The nerve cuff may include a cuff body affixed to the distal end of the lead body, a first row of electrically conductive members carried by the cuff body, spaced from one another in the width direction, and defining first and second lateral ends that are spaced apart from one another in the width direction and first and second longitudinal ends that are spaced apart from one another in the length direction, a first undulating conductor that connects the electrically conductive members in the first row to one another in series, that is connected to each of the conductive members at only one location by a joint that is located at one of the lateral ends of the conductive member, and that includes a plurality first regions that extend along the conductive members in the length direction and a plurality of second regions that extend from one first region to another first region in the width direction, a second row of electrically conductive members carried by the cuff body, spaced from one another in the width direction, a third row of electrically conductive members carried by the cuff body that are spaced from one another in the width direction, the third row being located between the first and second rows, and a plurality of electrical conductors extending through the lead body from at least some of the electrically conductive members to the proximal end of the lead body.

The present inventions also include systems with an implantable pulse generator or other implantable stimulation device in combination with such an electrode lead.

BRIEF DESCRIPTION OF THE DRAWINGS

Detailed descriptions of exemplary embodiments will be made with reference to the accompanying drawings.

DETAILED DESCRIPTION OF THE EXEMPLARY EMBODIMENTS

The following is a detailed description of the best presently known modes of carrying out the inventions. This description is not to be taken in a limiting sense, but is made merely for the purpose of illustrating the general principles of the inventions.

Figure 1:
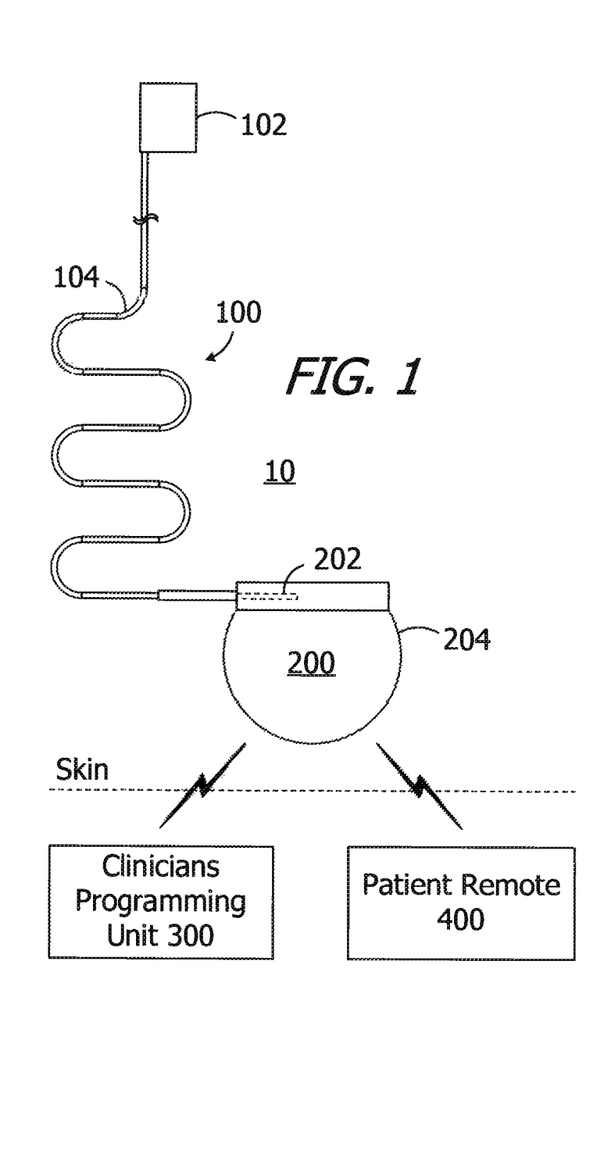
FIG. 1 is a plan view of a stimulation system in accordance with one embodiment of a present invention.
Figure 2:
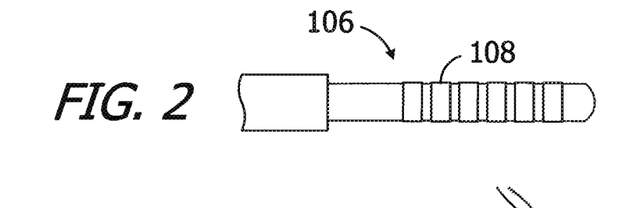
FIG. 2 is a plan view of a portion of the stimulation system illustrated in FIG. 1.

Referring to FIGS. 1 and 2, a stimulation system 10 in accordance with one embodiment of a present invention includes an electrode lead 100 and an implantable stimulator such as the implantable pulse generator ("IPG") 200. A clinician's programming unit 300, a patient remote 400 and an IPG charger (not shown) may also be provided in some instances. The exemplary electrode lead 100 includes a nerve cuff 102 and a lead body 104 that couples the nerve cuff 102 to the IPG 200 by way of lead connector 106, with a plurality contacts 108, on the proximal end of the lead body 104 and a corresponding connector receptacle 202 on the IPG 200. The nerve cuff 102 is configured in such a manner that it may be circumferentially disposed around either the HGN trunk or a HGN branch (e.g., the HGN GM branch) as is discussed below with reference to FIGS. 3 and 4. The lead body 104 may include one or more S-shaped sections in order to provide strain relief (as shown) or may be straight. The S-shaped sections accommodate body movement at the location within the neck where the lead body 104 is implanted, thereby reducing the likelihood that the HGN will be damaged due to unavoidable pulling of the electrode lead 100 that may result from neck movements. The accommodation provided by the S-shaped sections also reduces the likelihood of fatigue damage. Additionally, although the exemplary system 10 includes a single electrode lead 100, other embodiments may include a pair of electrode leads 100 for bilateral HGN stimulation and an IPG (not shown) with two connector receptacles.

Figure 3:
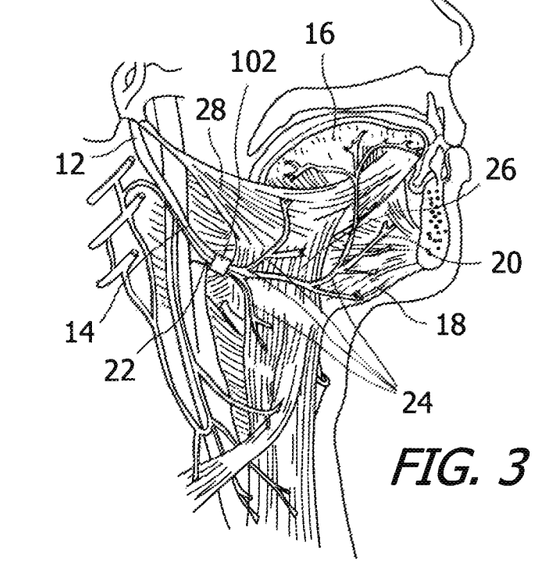
FIG. 3 is a cut-away anatomical drawing of the head and neck area illustrating the muscles that control movement of the tongue, the HGN and its branches that innervate these muscles, and the nerve cuff illustrated in FIG. 1 on the HGN trunk.
Figure 4:
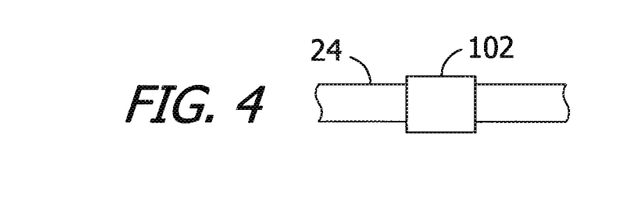
FIG. 4 is a plan view showing the nerve cuff illustrated in FIG. 1 on the HGN GM branch.

Turning to FIG. 3, and as alluded to above, the nerve cuff 102 may be positioned around the trunk 14 of the HGN 12 and used to stimulate the muscles that anteriorly move the tongue 16 and, in particular, the fascicles of the HGN 12 that innervate the tongue protrusor muscles, such as the genioglossus 18 and/or the geniohyoid muscles 20. The nerve cuff 102 is positioned on the HGN trunk 14 at a position 22 proximal to the HGN branches 24. Although there are advantages to implanting the nerve cuff 102 at this proximal position 22, i.e., reduced surgical time and effort as well as reduced risk and trauma to the patient, it introduces the problem of inadvertently stimulating other fascicles of the HGN trunk 14 that innervate muscles in opposition to the genioglossus 18 and/or the geniohyoid muscles 20, i.e., the tongue retractor muscles, e.g., the hyoglossus 26 and styloglossus muscles 28, as well as the intrinsic muscles of the tongue 16. Accordingly, while some clinicians may desire to stimulate the HGN 12 at the HGN trunk 14, others may desire to stimulate the HGN at the GM branch 24. As illustrated in FIG. 4, the same nerve cuff 102 is configured in such a manner that it may be positioned the HGN GM branch 24 instead of the trunk 14.

Figure 5:
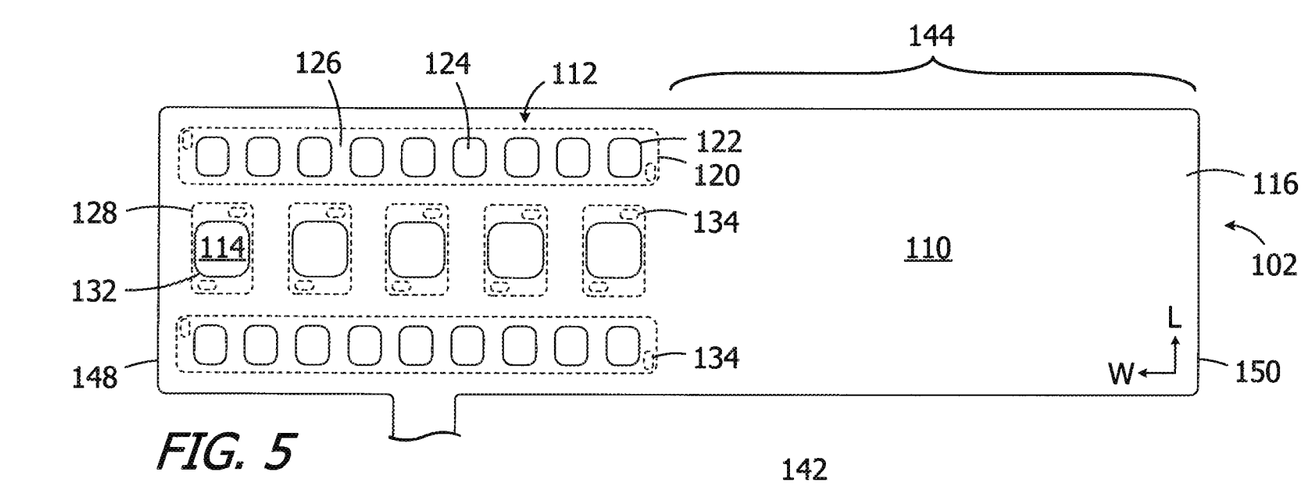
FIG. 5 is a front view of the nerve cuff illustrated in FIG. 1 in an unfurled state.
Figure 6:
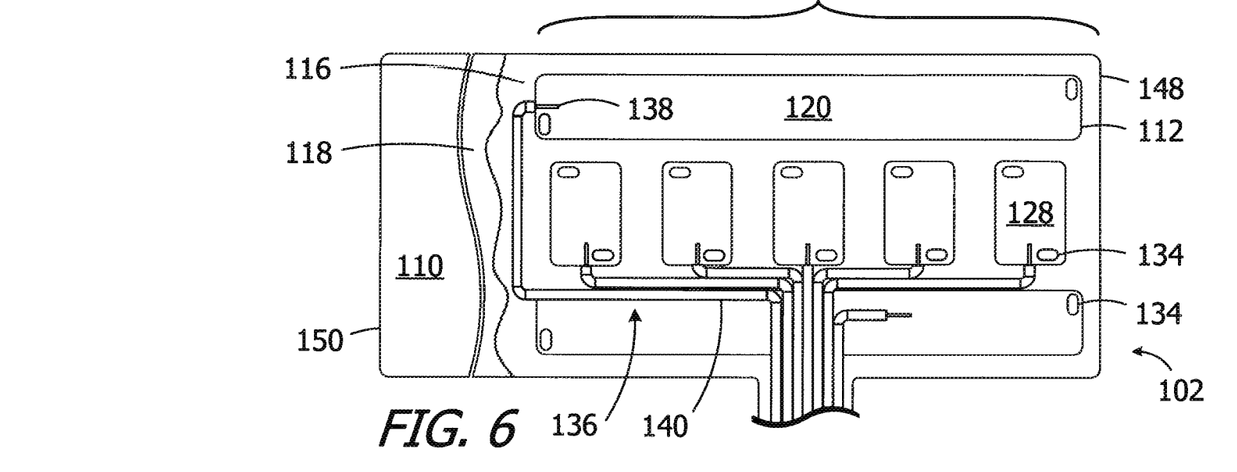
FIG. 6 is a rear, cutaway view of the nerve cuff illustrated in FIG. 1 in an unfurled state.
Figure 7:
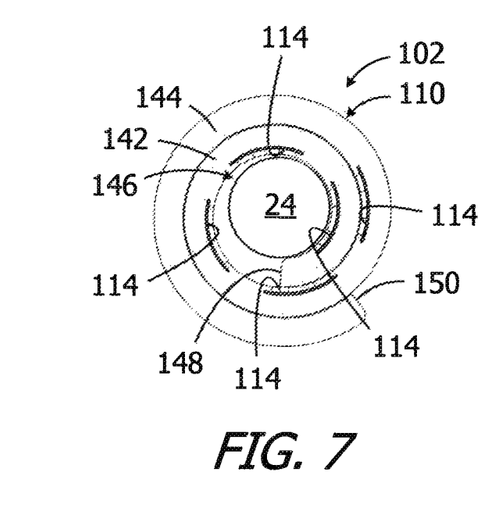
FIG. 7 is a section view of the nerve cuff illustrated in FIG. 1 in a pre-shaped furled state around a HGN branch.
Figure 8:
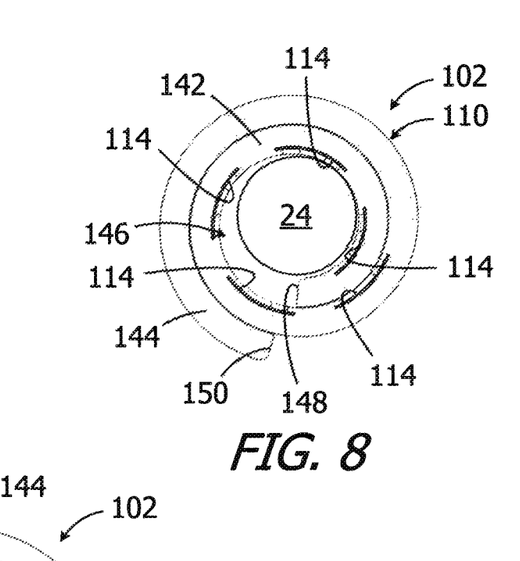
FIG. 8 is a section view of the nerve cuff illustrated in FIG. 1 in an expanded and less tightly furled state around a HGN branch.
Figure 9:
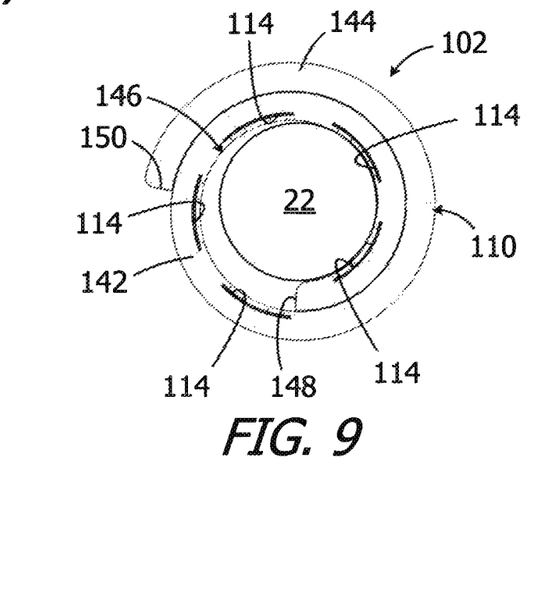
FIG. 9 is a section view of the nerve cuff illustrated in FIG. 1 in an expanded and less tightly furled state around a HGN trunk.

The exemplary nerve cuff 102 is shown in a flattened, unfurled state in FIGS. 5 and 6 and is shown in various furled states illustrated in FIGS. 7-9 that the nerve cuff will be in when it wraps around an HGN trunk 14 or HGN GM branch 24. In the illustrated implementation, the nerve cuff 102 is pre-set (or "pre-shaped") to the furled (or "curled") state illustrated in FIG. 7, and an external force may be used to partially or completely unfurl the nerve cuff 102. The nerve cuff 102 will return to the pre-shaped furled state when the force is removed and, as discussed below, may assume one of the furled states illustrated in FIGS. 7-9 depending on the size of the HGN trunk or HGN branch that the nerve cuff 102 is placed around. Various examples of nerve cuffs that are capable of assuming different sizes are disclosed in aforementioned U.S. Pat. Pub. No. 2019/0060646A1.

Referring first to FIGS. 5 and 6, the nerve cuff 102 includes a cuff body 110 that defines a length L and a width W that is greater than the length, first and second relatively wide electrically conductive contacts (or "relatively wide contacts") 112 on the cuff body 110 that extend in the width direction and are spaced from one another in the length direction and a plurality of relatively narrow electrically conductive contacts (or "relatively narrow contacts") 114. Such contacts may also be referred to as "electrodes." Although the number may increase or decrease in the context of other nerve applications, at least five relatively narrow contacts 114 may be spaced from one another in the width direction are located between the first and second relatively wide contacts 112, and there are five relatively narrow contacts 114 in the illustrated embodiment. As used herein, "relatively wide" structures are structures that are longer in the width direction than structures that are referred to as "relatively narrow" and "relatively narrow" structures are structures that are shorter in the width direction than structures that are referred to as "relatively wide." In the implementation illustrated in FIGS. 5 and 6, the relatively narrow contacts 114 are centered relative to the relatively wide contacts 112 and are aligned with one another in the length direction. In other implementations, the relatively narrow contacts may be non-centered relative to the relatively wide contacts 112 and/or offset from one another in the length direction. With respect to shape, and although the present inventions are not so limited, the relatively wide contacts 112 are in the shape of rectangles with rounded corners, while the relatively narrow contacts 114 are squares with rounded corners. Other exemplary shapes for the relatively wide contacts 112 include, but are not limited to, rounded rectangles and ellipses, while other exemplary shapes for the relatively narrow contacts 114 include, but are not limited to, circles, ellipses, squares, and rectangles.

The contacts 112 and 114 may be of any suitable construction. In the illustrated implementation, the cuff body 110 includes a front layer 116 that will face the HGN trunk or branch and a rear layer 118 that will face away from the HGN trunk or branch. With respect to the relatively wide contacts 112, the exemplary nerve cuff 102 includes first and second relatively wide conductive members 120 are located between the front layer 116 and rear layer 118. The relatively wide conductive members 120 are each exposed by way of respective pluralities of closely spaced openings 122 in the cuff body front layer 116. The openings 122 are located inwardly of the outer perimeter of the conductive members 120, which are shown in dashed lines in FIG. 5. The openings 122 define a plurality of exposed regions 124 and a plurality of straps 126 (discussed below) therebetween. There are two sets of exposed regions 124, the sets being separated by the relatively narrow contacts 114, and the exposed regions 124 in each set together function as a single contact (i.e., one of the contacts 112) because all of the exposed regions in each set are part of the same conductive member 120. With respect to the relatively narrow contacts 114, the exemplary nerve cuff 102 includes five relatively narrow conductive members 128 are located between the front layer 116 and rear layer 118. Portions of the relatively narrow conductive members 128 are exposed by way of respective relatively narrow openings 132 in the cuff body front layer 116, thereby defining the contacts 114. The openings 122 and 132 extend from the outer surface of the front layer 116 to the associated conductive members 120 and 128. The conductive members 120 and 128 may also include apertures 134 that, in conjunction with the material that forms the cuff body layers 116 and 118 and enters the apertures, anchor the conductive members in their intended locations.

There are a number of advantages associated with the exemplary straps 126 that are located between the openings 122. For example, as compared to an otherwise identical nerve cuff where each of the relatively wide conductive members is exposed by way of a single relatively wide opening that extends through the front layer of the cuff body and covers a narrow portion of the conductive member at the perimeter of the conductive member, the plurality of straps 126 extend across the conductive members in the length direction and increase the amount of the front layer that covers, restrains and is bonded to the conductive members 120 and, accordingly, reduce the likelihood of delamination. Additional techniques, such as plasma, primer, and surface roughening, may also be employed to improve adhesion and further reduce the likelihood of delamination as the nerve cuff is manipulated.

The contacts 112 and 114 in the illustrated embodiment may be individually electrically connected to the plurality contacts 108 on the lead connector 106 (FIG. 2) by wires 136 (FIG. 6) that extend through the lead body 104. Each wire 136 includes a conductor 138 and an insulator 140. The conductors 138 may be connected to the rear side of the conductive members 120 and 128 by welding or other suitable processes. In other implementations, the contacts 112 may also be electrically connected to one another by a short wire. Here, only one of the contacts 112 will be connected to a contact 108 on the lead connector 106 by way of a wire 136. It should also be noted that, in the exemplary nerve cuff 102 (as well as the nerve cuffs 102a-102e described below), the contacts 114 are not electrically connected in series to one another and are each connected to a respective one of the wires 136. In other implementations, cables may be employed in place of the wires 136.

The cuff body 110 in the exemplary implementation illustrated in FIGS. 5 and 6 includes a stimulation region 142 and a compression region 144. The contacts 112 and 114 are located within the stimulation region 142. There are no contacts located within the compression region 144. The compression region 144 wraps around at least a portion of the stimulation region 142 when the nerve cuff 102 is in the pre-shaped furled state and the slightly larger, expanded and less tightly furled states described below with reference to FIGS. 7-9, thereby resisting (but not preventing) expansion of the stimulation region and improving the electrical connection between the contacts 112 and 114 and the HGN.

The exemplary cuff body 110 may be formed from any suitable material. Such materials may be biologically compatible, electrically insulative, elastic and capable of functioning in the manner described herein. By way of example, but not limitation, suitable cuff body materials include silicone, polyurethane and styrene-isobutylene-styrene (SIBS) elastomers. Suitable materials for the contacts 112 and 114 include, but are not limited to, platinum-iridium and palladium. The cuff materials should be pliable enough to allow a clinician to unfurl the cuff body 110 (and nerve cuff 102) and place the nerve cuff around the HGN trunk (or HGN GM branch), The exemplary materials should also be resilient enough to cause the nerve cuff return to the pre-shaped furled state illustrated in FIG. 7 when the force is removed, yet flexible enough to allow the cuff body 110 (and nerve cuff 102) to instead assume the slightly larger, expanded and less tightly furled states illustrated in FIGS. 8 and 9. To that end, the furled cuff body 110 defines an inner lumen 146, in which the nerve will be located after the nerve cuff 102 wraps around the nerve, as well as lateral ends 148 and 150, which may be tapered in some implementations to reduce tissue irritation, that are respectively associated with the stimulation region 142 and the compression region 144. Comparing the state illustrated in FIG. 8 to that state illustrated in FIG. 7, the inner lumen 146 is slightly larger and the lateral end 150 is offset around the perimeter of the nerve cuff 102. Similarly, comparing the state illustrated in FIG. 9 to that state illustrated in FIG. 8, the inner lumen 146 is slightly larger and the lateral end 150 is offset around the perimeter of the nerve cuff 102. For example, the inner lumen 146 in FIG. 7 is sized to accommodate an HGN structure that has a diameter of about 2.5 mm (e.g., the HGN GM branch 24), the inner lumen 146 in FIG. 8 is sized to accommodate an HGN structure that has a diameter of about 3.0 mm (e.g., the HGN GM branch 24 in a swollen state), and the inner lumen 146 in FIG. 9 is sized to accommodate an HGN structure that has a diameter of about 4.0 mm (e.g., the HGN trunk 22). The ability to assume slightly larger, expanded and less tightly furled states, in addition to the smaller fully furled state, allows the same nerve cuff 102 to accommodate either of the larger HGN trunk 14 or a smaller HGN branch 24. The ability to assume slightly larger; expanded furled states also allows the nerve cuff to accommodate nerve swelling that may occur post-surgery and to self-adjust to a smaller state when the swelling subsides.

It should also be noted here that the relatively wide contacts 112 are sized such that they extend completely around the inner lumen 146, i.e., 360° or more around the longitudinal axis of the inner lumen, when the cuff body 110 is in the fully furled state illustrated in FIG. 7 that accommodates an HGN structure having a diameter of about 2.5 mm. Viewed as a group, the relatively narrow contacts 114 also extend completely around the inner lumen 146 when the when the cuff body 110 is in the fully furled state illustrated in FIG. 7. The relatively wide contacts 112 also extend substantially around the inner lumen 146, i.e., at least 288 in some examples and 360° or more in other examples, around the longitudinal axis of the inner lumen, when the cuff body 110 is in the expanded and less tightly furled state illustrated in FIG. 9 that accommodates an HGN structure having a diameter of about 4.0 mm. Viewed as a group, the relatively narrow contacts 114 also extend substantially around the inner lumen 146 when the when the cuff body 110 is in the expanded and less tightly furled state illustrated in FIG. 9.

Figure 10:
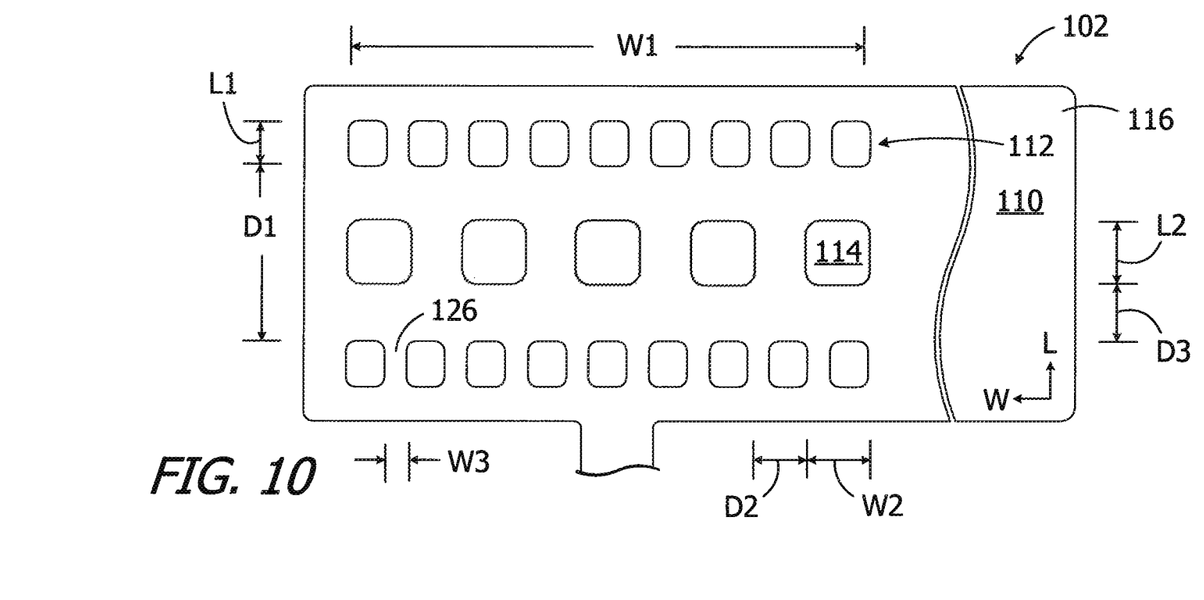
FIG. 10 is a front view of the nerve cuff illustrated in FIG. 1 in an unfurled state.

The dimensions of the present nerve cuffs, including the various elements thereof, may by any dimensions that result in the nerve cuffs functioning as intended. With respect to the dimensions of the cuff body 110 of the exemplary nerve cuff 102, and referring to FIG. 5, the cuff body is about 1.1 inches wide and about 0.34 inches long. As used herein in the context of dimensions, the word "about" means±10-20%. The width of the stimulation region 142 is about 0.6 inches, while the width of the compression region 144 is about 0.5 inches. The relatively wide contacts 112 are same size, and the relatively narrow contacts 114 are the same size, in the illustrated implementation. In other implementations, the relatively wide contacts 112 may be different sizes and/or the relatively narrow contacts 114 may be different sizes. Referring to FIG. 10, the width W1 of the relatively wide contacts 112 is about 0.5 inches, the length L1 is about 0.04 inches, the distance D1 between the relatively wide contacts 112 is about 0.2 inches, and the width W3 of the straps 126 is about 0.02 inches. The width W2 of the relatively narrow contacts 114 is about 0.07 inches, the length L2 is about 0.06 inches and the distance D2 between the relatively narrow contacts 114 is about 0.05 inches. The distance D2 may also be increased or decreased as desired to accomplish various stimulation objectives. The distance D3 between the relatively narrow contacts 114 and the relatively wide contacts 112 is about 0.07 inches.

Figure 11:
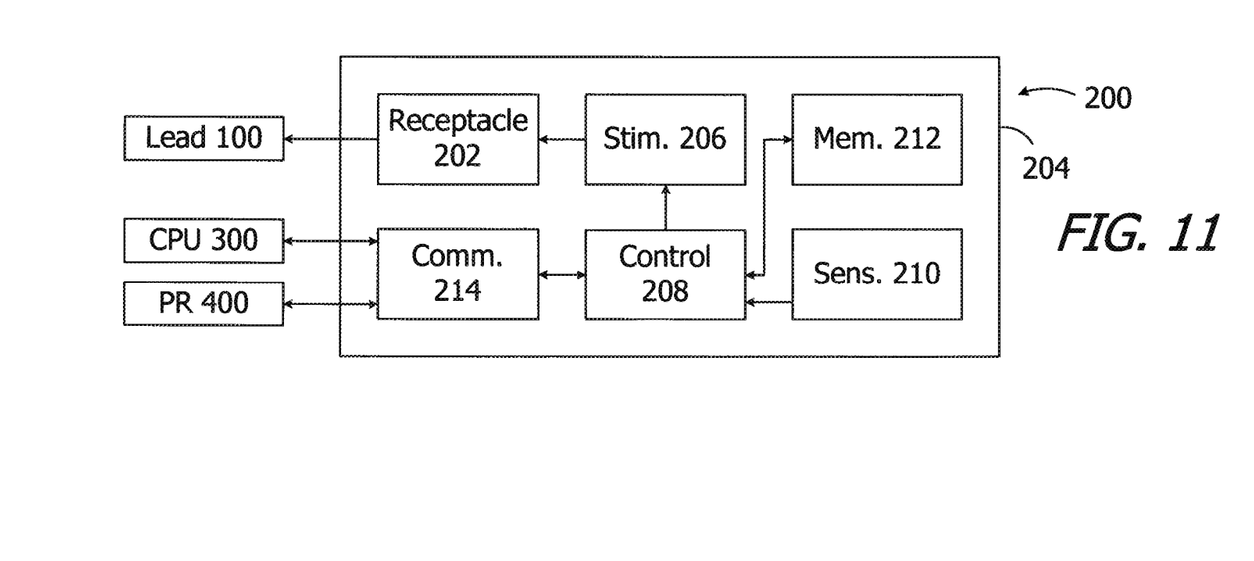
FIG. 11 is a block diagram of the stimulation system illustrated in FIG. 1.

Turning to FIG. 11, the exemplary IPG 200 includes the aforementioned receptacle 202, a hermetically sealed outer case 204, and various circuitry (e.g., stimulation circuitry 206, control circuitry 208, sensing circuitry 210, memory 212, and communication circuitry 214) that is located within the outer case 204. The outer case 204 may be formed from an electrically conductive, biocompatible material such as titanium. The stimulation circuitry 206, which is coupled to the contacts 112 and 114 by way of the connector 106, receptacle 202 and wires 136, is configured to deliver stimulation energy to the HGN. The control circuitry 208 controls when and for how long the stimulation circuitry 206 applies stimulation, the intensity of the stimulation, the mode of stimulation (i.e., monopolar, bipolar or tripolar), and the particular contacts that are used in the stimulation. In the monopolar stimulation, at least a portion of the outer case 204 functions as a return electrode in the electrical circuit that also includes one or more of the contacts 112 and 114. In bipolar stimulation, the outer case 204 is not part of the electrical circuit and current instead flows from one of the contacts 112 and 114 to one of the other contacts 112 and 114. In tripolar stimulation, the outer case 204 is not part of the electrical circuit and current flows from one or more of the contacts 112 and 114 to more than one of the other contacts 112 and 114. The contacts that the current flows to form part of the return path for the stimulation energy, as do the associated wires connected thereto. The stimulation may also be predominantly axial vector stimulation, predominantly radial vector stimulation, or a hybrid of axial vector and radial vector.

It should also be noted here that in most instances, contacts that are entirely separated from (and electrically disconnected from) the associated nerve by the cuff body will not be used by the IPG for current transmission and return. For example, when the exemplary nerve cuff 102 is in less lightly furled state illustrated in FIG. 8, one of the contacts 114 is entirely separated from the GM branch 24 by the electrically non-conductive cuff body 110 and will not be used for current transmission or return. Such contacts may be identified by, for example, measuring the impedance at each contact.

The sensing circuitry 210 in the illustrated embodiment may be connected to one or more sensors (not shown) that are contained within the outer case 204. Alternatively, or in addition, the sensors may be affixed to the exterior of the outer case 204 or positioned at a remote site within the body and coupled to the IPG 200 with a connecting lead. The sensing circuitry 210 can detect physiological artifacts that are caused by respiration (e.g., motion or ribcage movement), which are proxies for respiratory phases, such as inspiration and expiration or, if no movement occurs, to indicate when breathing stops. Suitable sensors include, but are not limited to, inertial sensors, bioimpedance sensors, pressure sensors, gyroscopes, ECG electrodes, temperature sensors, GPS sensors, and combinations thereof. The memory 212 stores data gathered by the sensing circuitry 210, programming instructions and stimulation parameters. The control circuitry 208 analyzes the sensed data to determine when stimulation should be delivered. The communication circuitry 214 is configured to wirelessly communicates with the clinician's programming unit 300 and patient remote 400 using radio frequency signals.

The control circuitry 208 may apply stimulation energy to either the HGN truck or an HGN branch (e.g, the HGN GM branch) in various stimulation methodologies by way of the cuff 102 when the patient is in the inspiratory phase of respiration; and other conditions for stimulation are met, thereby causing anterior displacement of the tongue to keep the upper airway unobstructed. The control circuitry 208 causes the stimulation circuitry 206 to apply stimulation in the form of a train of stimulation pulses during these inspiratory phases of the respiratory cycle (or slightly before the inspiration and ending at the end of inspiration) and not the remainder of the respiration cycle. The train of stimulus pulses may be set to a constant time duration or may change dynamically based on a predictive algorithm that determines the duration of the inspiratory phase of the respiratory cycle.

Figure 12:
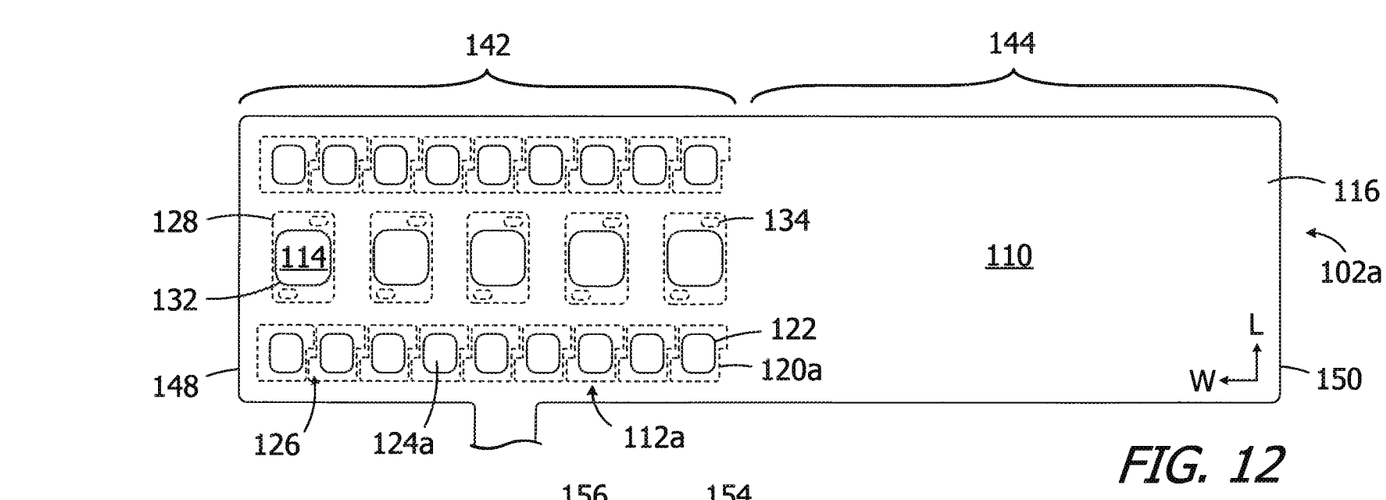
FIG. 12 is a front view of a nerve cuff in accordance with one embodiment of a present invention in an unfurled state.
Figure 13:
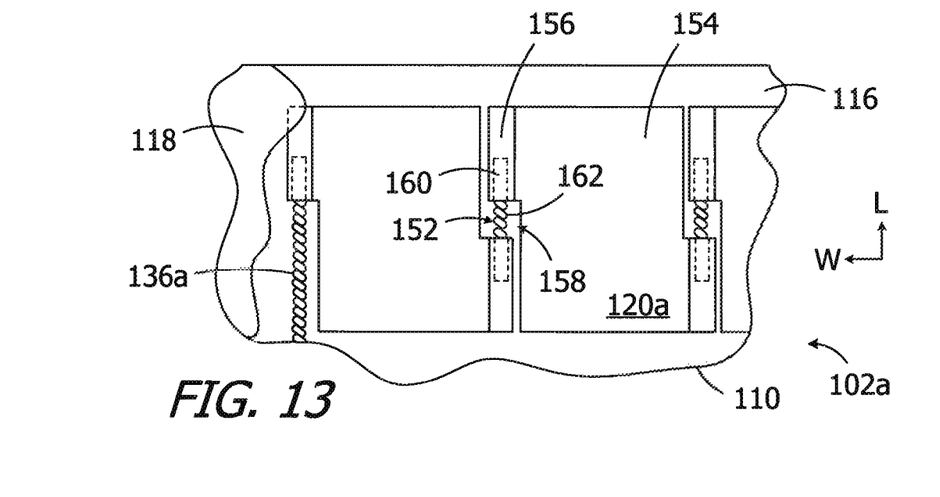
FIG. 13 is a rear, cutaway view of a portion of the nerve cuff illustrated in FIG. 12 in an unfurled state.

Another exemplary nerve cuff is generally represented by reference numeral 102a in FIGS. 12 and 13. Nerve cuff 102a is substantially similar to nerve cuff 102 and similar elements are represented by similar reference numerals. For example, the nerve cuff 102a may form part of an electrode lead that may be connected to the IPG 200, or other suitable device, and employed in stimulation methodologies such as those described above. The nerve cuff 102a includes a cuff body 110 with a front layer 116, a rear layer 118, two relatively wide contacts 112a, and a plurality of relatively narrow contacts 114 that are defined by portions of the relatively narrow conductive members 128 that are exposed by way of respective relatively narrow openings 132 in the cuff body front layer 116. The cuff body 110 also has a stimulation region 142 and a compression region 144. The contacts 112a and 114 may be individually electrically connected to the plurality contacts 108 on the lead connector 106 (FIG. 2) by wires that extend through the lead body 104 in the manner described above with reference to FIG. 6. Here, however, each relatively wide contact 112a includes a plurality of spaced conductive members 120a that are electrically connected to one another in series and together function in a manner similar to a single, unitary conductive member (e.g., conductive member 120). The conductive members 120a have portions 124a that are exposed by way of openings 122 in the cuff body front layer 116. The straps 126 therebetween advantageously function in the manner described above.

Referring more specifically to FIG. 13, the conductive members 120a in each contact 112a may be connected to one another by flexible conductors 152 such as, for example, conductive coils (as shown), wires, or braided cables. In the illustrated implementation, the flexible conductors 152 extend in the length direction L of the cuff body 110. As used herein, a flexible conductor that extends in the length direction of the cuff body 110 is a flexible conductor that defines a diameter (or width) as well as a length that is greater than the diameter (or width) and the length of the flexible conductor is parallel to or at least substantially parallel to (i.e., ±5° from parallel to) the length direction L of the cuff body. The conductive members 120a include a main body 154 and a pair of crimp regions 156 that extend from the main body 154 in the width direction W of the cuff body 110. A gap 158 is defined between the crimp regions 156. The ends 160 of the flexible conductors 152 are crimped to the conductive members 120a at the crimp regions 156 and an uncrimped portion 162 of the flexible conductors is located within the gap 158 between the crimp regions. The uncrimped portion of the flexible conductors 152 accommodates the torsion force applied thereto as the nerve cuff moves in and out of its pre-set furled state. In at least some implementations, conductive coils or other flexible conductors 136a that extend to the lead connector 106 (FIG. 2) may be employed in place of the above-described wires 136.

The use of a plurality of spaced, electrically connected conductive members 120a increases the flexibility of the contacts 112a, as compared to otherwise similar contacts that include a single conductive member, thereby increasing the flexibility of the nerve cuff as it moves in and out of its pre-set furled state.

Figure 14:
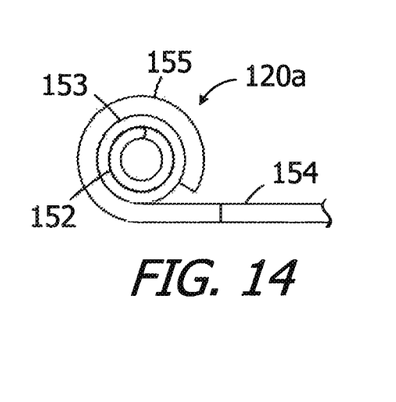
FIG. 14 is a side view of a conductive member prior to being crimped.

With respect to the crimping process, crimp tubes 153 (FIG. 14) may be provided on the ends 160 of the flexible conductors 152 and the conductive members 120a may be provided with rolled portions 155 into which the conductor ends and crimp tubes are inserted prior to crimping and the formation of the crimp regions 156. In other instances, and as described below with reference to FIGS. 21-23A, portions of the conductive members may include a crimp tabs that are rolled or folded over the crimp tubes 153 and coil ends 160 prior to crimping and the formation of the crimp regions. The exemplary flexible conductors 152 may include a conductor and an insulator, or simply a conductor. In those instances where the conductive coils 152 include a conductor and an insulator, the portions of the insulators within the crimp regions may be removed prior to crimping or simply allowed to squeeze out of the resulting joint during the crimping process. Other exemplary methods of securing the flexible conductors 152 to conductive members 120a include, but are not limited to, forming joints by welding and combined welding/crimping processes.

Figure 15:
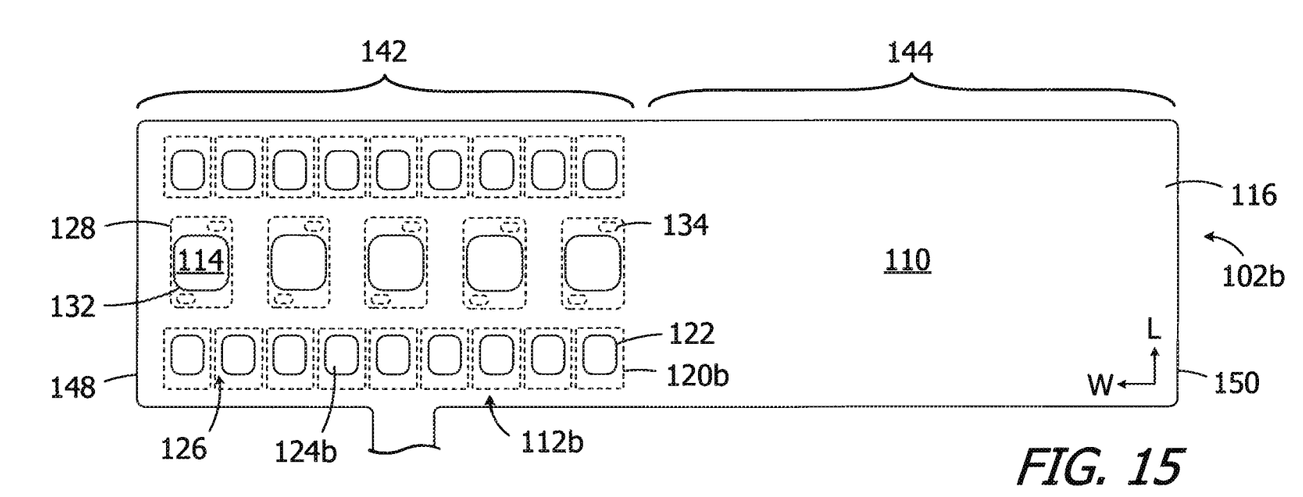
FIG. 15 is a front view of a nerve cuff in accordance with one embodiment of a present invention in an unfurled state.
Figure 16:
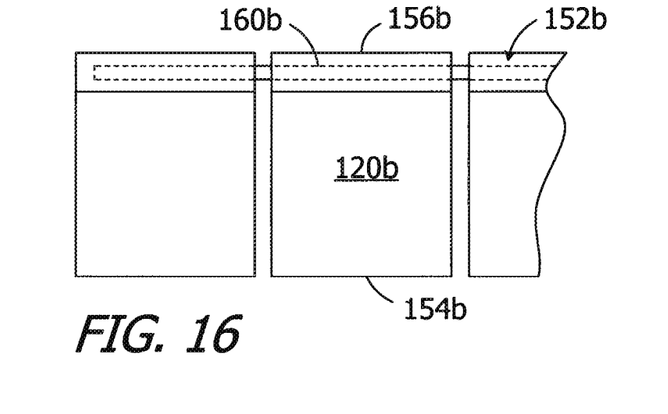
FIG. 16 is a rear view of a portion of the nerve cuff illustrated in FIG. 15.

Another exemplary nerve cuff is generally represented by reference numeral 102b in FIGS. 15 and 16. Nerve cuff 102b is substantially similar to nerve cuff 102 and similar elements are represented by similar reference numerals. For example, the nerve cuff 102b may form part of an electrode lead that may be connected to the IPG 200, or other suitable device, and employed in stimulation methodologies such as those described above. The nerve cuff 102b includes a cuff body 110 with a front layer 116, a rear layer 118, two relatively wide contacts 112b, and a plurality of relatively narrow contacts 114 that are defined by portions of the relatively narrow conductive members 128 that are exposed by way of respective relatively narrow openings 132 in the cuff body front layer 116. The cuff body 110 also has a stimulation region 142 and a compression region 144. The contacts 112b and 114 may be individually electrically connected to the plurality contacts 108 on the lead connector 106 (FIG. 2) by wires that extend through the lead body 104 in the manner described above with reference to FIG. 6. Here, however, each relatively wide contact 112b includes a plurality of spaced conductive members 120b that are electrically connected to one another in series and together function in a manner similar to a single, unitary conductive member (e.g., conductive member 120). The conductive members 120b have portions 124b that are exposed by way of openings 122 in the cuff body front layer 116. The straps 126 therebetween advantageously function in the manner described above.

Referring more specifically to FIG. 16, the conductive members 120b in each contact 112b may be connected to one another in series by, for example, a conductive braided cable 152b (as shown), a coil, or a wire. In the illustrated implementation, the conductive cable 152b extends in the width direction W of the cuff body 110. As used herein, a conductive cable that extends in the width direction of the cuff body 110 is a conductive cable that defines a diameter (or width) as well as a length that is greater than the diameter (or width) and the length of the conductive cable is parallel to or at least substantially parallel to (i.e., ±5° from parallel to) the width direction W of the cuff body. The conductive members 120b include a main body 154b, defining a length in the length direction L of the cuff body 110 and a width in the width direction W, and a single crimp region 156b at one of the longitudinal ends of the main body. In the exemplary nerve cuff 102b, the crimp regions 156b are all at the same longitudinal end. Portions 160b of the conductive cable 152b are crimped to the conductive members 120b at the crimp regions 156b.

The use of a plurality of spaced, electrically connected conductive members 120b increases the flexibility of the contacts 112b, as compared to otherwise similar contacts that include a single conductive member, thereby increasing the flexibility of the nerve cuff as it moves in and out of its pre-set furled state.

Figure 17:
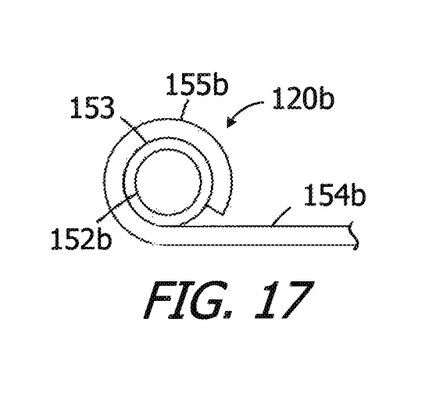
FIG. 17 is a side view of a conductive member prior to being crimped.

With respect to the crimping process, crimp tubes 153 (FIG. 17) may be provided at spaced locations along the conductors 156b and the conductive members 120b may be provided with rolled portions 155 through which the conductive cable 152b is passed prior to crimping and the formation of the crimp regions 156b. It should be noted here that positioning a rolled portion 155 at the longitudinal end of the conductive member 120b reduces the complexity of the manufacturing process, as compared to a process where the structure that receives the cable is located in the middle region of the conductive member. A first cable 152b connects each of the conductive members 120b in one of the contacts 112b to one another in series, while a second cable 152b connects each of the conductive members 120b in the other contact 112b to one another in series. In other instances, and as described below with reference to FIGS. 21-23A, the conductive members may each include a crimp tab that is rolled or folded over the crimp tubes 153 and cable portions 160b prior to crimping and the formation of the crimp regions. The exemplary conductive cables 152b may include a conductor and an insulator, or simply a conductor. In those instances where the conductive cables 152b include a conductor and an insulator, portions of the insulators within the crimp regions may be removed prior to crimping or simply squeeze out of the resulting joint during the crimping process. Other exemplary methods of securing the flexible conductors 152b to conductive members 120b include, but are not limited to, forming joints by welding and combined welding/crimping processes.

The contacts 112b and 114 may be individually electrically connected to the plurality contacts 108 on the lead connector 106 (FIG. 2) by wires that extend through the lead body 104 in the manner described above with reference to FIG. 6. In at least some implementations, coiled wires may be employed.

Figure 18:
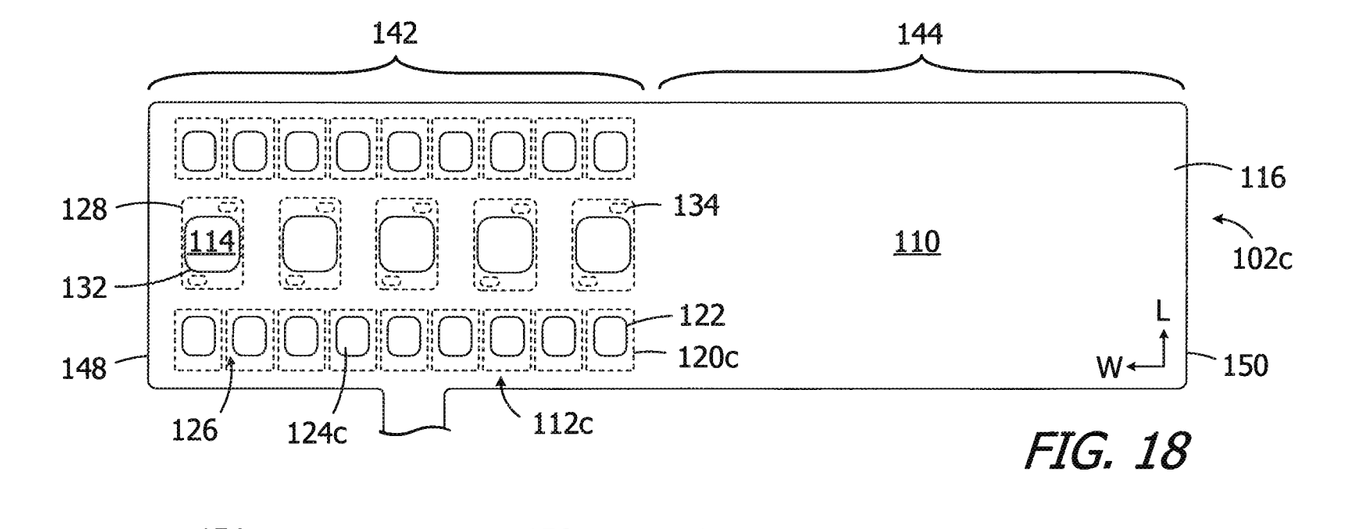
FIG. 18 is a front view of a nerve cuff in accordance with one embodiment of a present invention in an unfurled state.

Another exemplary nerve cuff is generally represented by reference numeral 102c in FIG. 18. Nerve cuff 102c is substantially similar to nerve cuff 102 and similar elements are represented by similar reference numerals. For example, the nerve cuff 102c may form part of an electrode lead that may be connected to the IPG 200, or other suitable device, and employed in stimulation methodologies such as those described above. The nerve cuff 102c includes a cuff body 110 with a front layer 116, a rear layer 118, two relatively wide contacts 112c, and a plurality of relatively narrow contacts 114 that are defined by portions of the relatively narrow conductive members 128 that are exposed by way of respective relatively narrow openings 132 in the cuff body front layer 116. The cuff body 110 also has a stimulation region 142 and a compression region 144. The contacts 112c and 114 may be individually electrically connected to the plurality contacts 108 on the lead connector 106 (FIG. 2) by wires that extend through the lead body 104 in the manner described above with reference to FIG. 6. Here, however, each relatively wide contact 112c includes a plurality of spaced conductive members 120c that are connected to one another in the manner described below with reference to FIG. 19 and that together function in a manner similar to a single, unitary conductive member (e.g., conductive member 120). The conductive members 120c have portions 124c that are exposed by way of openings 122 in the cuff body front layer 116. The straps 126 therebetween advantageously function in the manner described above.

Figure 19:
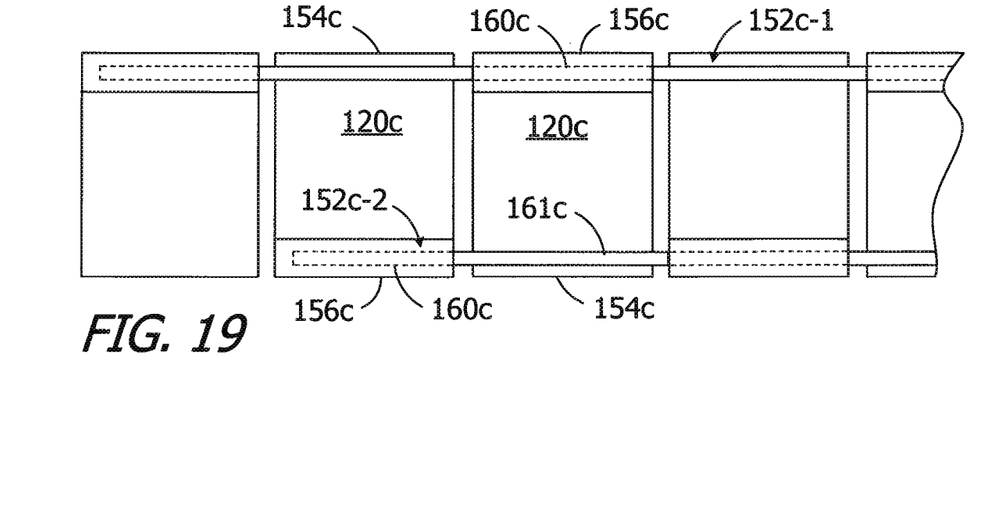
FIG. 19 is a rear view of a portion of the nerve cuff illustrated in FIG. 18.

Referring to FIG. 19, each contact 112c in the illustrated embodiment includes two sets of conductive members 120c arranged such that adjacent conductive members are in different sets. The conductive members 120c in each set are connected to one another in series by, for example, a conductive braided cable 152c (as shown), a coil, or a wire. As such, each contact 112c includes two conductive braided cables 152c-1 and 152c-2 that extend in the width direction and are respectively connected to different subsets of the conductive members 120c. Adjacent conductive members 120c are also oriented differently than one other, with the crimp regions 156c of adjacent conductive members being on opposite longitudinal ends of the main body 154c, to accommodate the two cables 152c-1 and 152c-2. Portions 160c of the conductive cables 152c-1 and 152c-2 are crimped to the conductive members 120c at the crimp regions 156c. Portions 161c of the conductive cables 152c-1 and 152c-2, which are located between the crimped portions 160c, pass over the conductive members 120c and are not crimped or otherwise secured to the conductive members.

The use of a plurality of spaced, electrically connected conductive members 120c increases the flexibility of the contacts 112c, as compared to otherwise similar contacts that include a single conductive member, thereby increasing the flexibility of the nerve cuff as it moves in and out of its pre-set furled state. Moreover, the alternating manner by which the contact members 120c are connected, and the corresponding increase in the distance between adjacent crimp regions, further increases the flexibility of the contacts 112c and resistance to fatigue failure.

With respect to the crimping process, crimp tubes 153 (FIG. 17) may be provided at spaced locations along the conductors 152c and the conductive members 120c may be provided with a rolled portion (e.g., rolled portion 155b in FIG. 17) through which a conductive cable 152c is passed prior to crimping and the formation of the crimp regions 156c. A first pair of cables 152c-1 and 152c-2 respectively connect alternating and oppositely oriented conductive members 120c to one another in one of the contacts 112c, while a second pair of cables 152c-1 and 152c-2 respectively connect alternating and oppositely oriented conductive members 120c to one another in the other contact 112c. In other instances, and as described below with reference to FIGS. 21-23A, the conductive members may include a crimp tab that is rolled or folded over the crimp tubes 153 (FIG. 17) and cable portions 160c prior to crimping and the formation of the crimp regions. The exemplary conductive cables 152c may include a conductor and an insulator and portions of the insulators within the crimp regions 156c may be removed prior to crimping or simply squeeze out of the resulting joint during the crimping process. Other exemplary methods of securing the flexible conductors 152c to conductive members 120c include, but are not limited to, joints that are formed by welding and combined welding/crimping processes.

Figure 20:
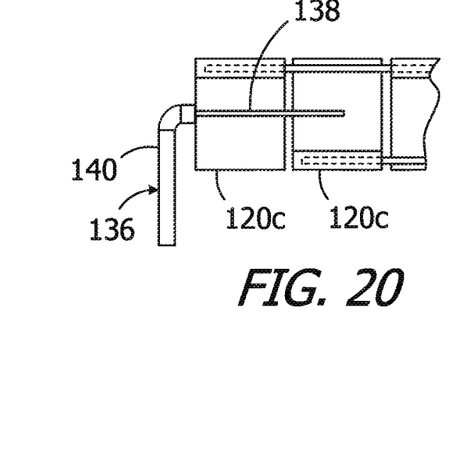
FIG. 20 is a rear view of a portion of the nerve cuff illustrated in FIG. 18.

The contacts 114 may be individually electrically connected to the plurality contacts 108 on the lead connector 106 (FIG. 2) by wires that extend through the lead body 104 in the manner described above with reference to FIG. 6. With respect to the contacts 112c, the wires 136 that are connected to the contacts 112c may be connected to two adjacent conductive members 120b in each contact welding or other suitable processes, as shown in FIG. 20.

Figure 21:
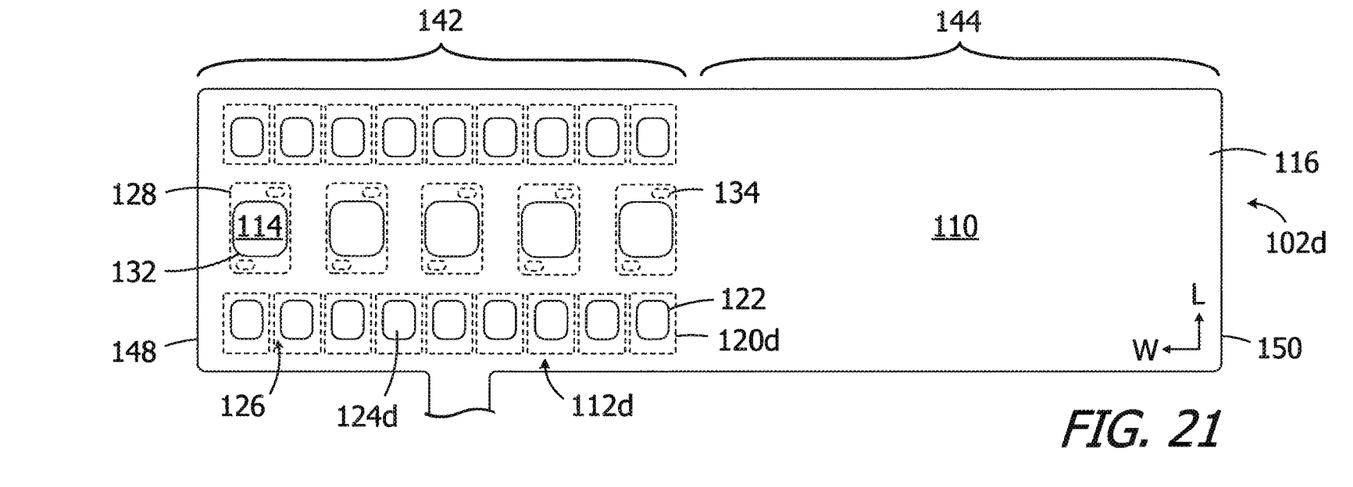
FIG. 21 is a front view of a nerve cuff in accordance with one embodiment of a present invention in an unfurled state.

Another exemplary nerve cuff is generally represented by reference numeral 102d in FIG. 21. Nerve cuff 102d is substantially similar to nerve cuff 102 and similar elements are represented by similar reference numerals. For example, the nerve cuff 102d may form part of an electrode lead that may be connected to the IPG 200, or other suitable device, and employed in stimulation methodologies such as those described above. The nerve cuff 102d includes a cuff body 110 with a front layer 116, a rear layer 118, two relatively wide contacts 112d and a plurality of relatively narrow contacts 114 that are defined by portions of the relatively narrow conductive members 128 that are exposed by way of respective relatively narrow openings 132 in the cuff body front layer 116. The cuff body 110 also has a stimulation region 142 and a compression region 144. The contacts 112d and 114 may be individually electrically connected to the plurality contacts 108 on the lead connector 106 (FIG. 2) by wires that extend through the lead body 104 in the manner described above with reference to FIG. 6. Here, however, each relatively wide contact 112d includes a plurality of spaced conductive members 120d that are electrically connected to one another in series. The conductive members 120d have portions 124d that are exposed by way of openings 122 in the cuff body front layer 116. The straps 126 therebetween advantageously function in the manner described above.

Figure 22:
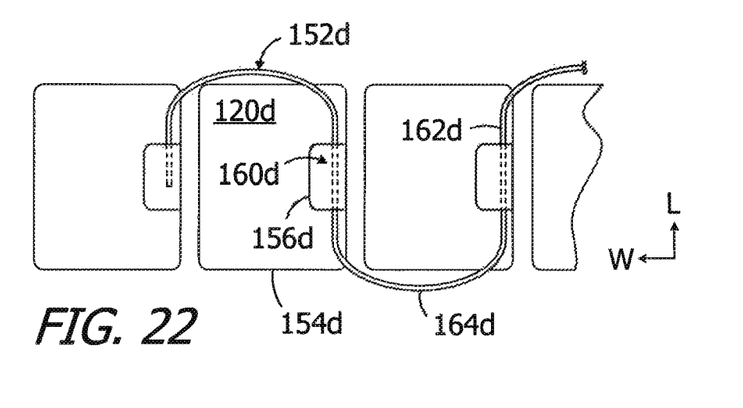
FIG. 22 is a rear view of a portion of the nerve cuff illustrated in FIG. 21.
Figure 23:
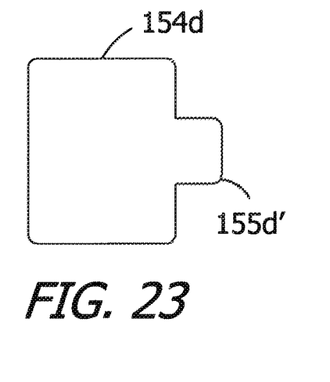
FIG. 23 is a rear view of a portion of the nerve cuff illustrated in FIG. 21 prior to rolling.
Figure 23A:
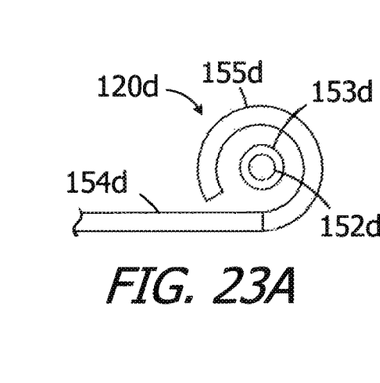
FIG. 23A is a side view of a portion of the nerve cuff illustrated in FIG. 21 prior to being crimped.

Referring to FIG. 22, the conductive members 120d of each contact 112d may be connected to one another by, for example, a conductive wire 152d (as shown), a coil, or a braided cable. In the illustrated implementation, the conductive members 120d include a main body 154d, with longitudinal ends in the length direction L and lateral ends in the width direction W, and a crimp region 156d. The conductive wire 152d extends from conductive member to conductive member in an undulating manner and includes regions 162d that extend in the length direction and regions 164d that extend in the width direction. Portions 160d of the conductive wire regions 162d that extend in the length direction are crimped to the conductive members 120d at the crimp regions 156d. In particular, the conductive wire 152d is crimped to each conductive member 120d at only a single location (i.e., crimp region 156d) that is adjacent to only one of the lateral ends of the conductive member. The length of the crimp regions 156d is less than the length of the conductive members 120d. The regions 164d that extend in the width direction are located adjacent to alternating longitudinal ends (i.e., alternating ends in the length direction) of the conductive members 120d.

The use of a plurality of spaced, electrically connected conductive members 120d increases the flexibility of the contacts 112d, as compared to otherwise similar contacts that include a single conductive member, thereby increasing the flexibility of the nerve cuff as it moves in and out of its pre-set furled state. The undulating shape of the wire 152d further increases the flexibility of the nerve cuff and reduces the likelihood of fatigue failure of the wire.

With respect to the crimping process, crimp tubes 153d (FIG. 23A) may be provided at spaced locations along the wires 152d and the conductive members 120d may be provided with a rolled portion 155d (FIG. 23A) through which the wire 152d passes. The conductive members 120d may be provided with a tab 155d' (FIG. 23) that is rolled or folded over the wire 152d, thereby forming the rolled portions 155d or similar folded portions, prior to crimping and the formation of the crimp regions 156d. The exemplary wires 152d may include a conductor and an insulator, or simply a conductor. In those instances where the wires 152d include a conductor and an insulator, portions of the insulators within the crimp regions may be removed prior to crimping or simply squeeze out of the resulting joint during the crimping process. Other exemplary methods of securing the flexible conductors 152d to conductive members 120d include, but are not limited to, joints that are formed by welding and combined welding/crimping processes.

The contacts 112d and 114 may be individually electrically connected to the plurality contacts 108 on the lead connector 106 (FIG. 2) by wires that extend through the lead body 104 in the manner described above with reference to FIG. 6. In at least some implementations, coiled wires may be employed.

Figure 24:
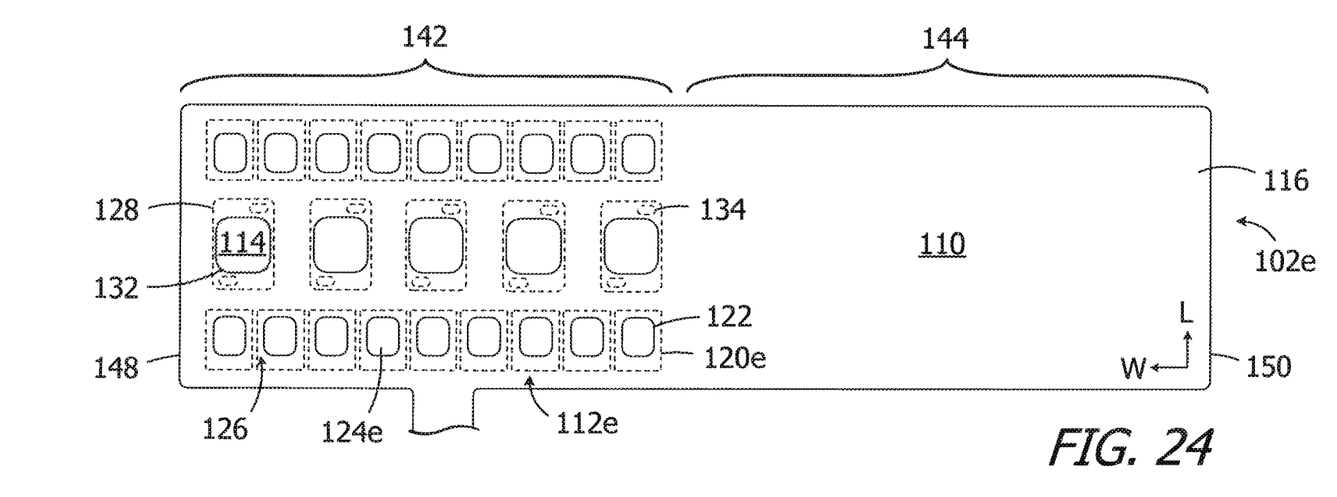
FIG. 24 is a front view of a nerve cuff in accordance with one embodiment of a present invention in an unfurled state.

Another exemplary nerve cuff is generally represented by reference numeral 102e in FIG. 24. Nerve cuff 102e is substantially similar to nerve cuff 102 and similar elements are represented by similar reference numerals. For example, the nerve cuff 102e may form part of an electrode lead that may be connected to the IPG 200, or other suitable device, and employed in stimulation methodologies such as those described above. The nerve cuff 102e includes a cuff body 110 with a front layer 116, a rear layer 118, two relatively wide contacts 112e and a plurality of relatively narrow contacts 114 that are defined by portions of the relatively narrow conductive members 128 that are exposed by way of respective relatively narrow openings 132 in the cuff body front layer 116. The cuff body 110 also has a stimulation region 142 and a compression region 144. The contacts 112e and 114 may be individually electrically connected to the plurality contacts 108 on the lead connector 106 (FIG. 2) by wires that extend through the lead body 104 in the manner described above with reference to FIG. 6. Here, however, each relatively wide contact 112e includes a plurality of spaced conductive members 120e that are electrically connected to one another in series. The conductive members 120e have portions 124e that are exposed by way of openings 122 in the cuff body front layer 116. The straps 126 therebetween advantageously function in the manner described above.

Figure 25:
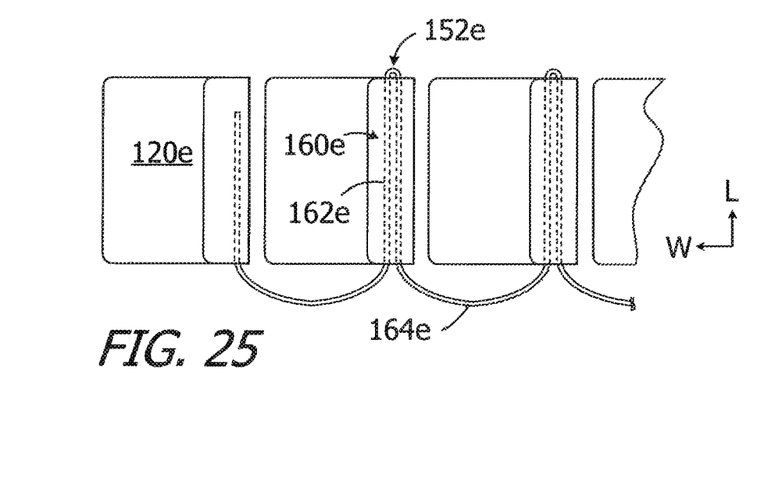
FIG. 25 is a rear view of a portion of the nerve cuff illustrated in FIG. 24.

Referring to FIG. 25, the conductive members 120e of each contact 112e may be connected to one another by, for example, a conductive wire 152e (as shown), a coil, or a braided cable. In the illustrated implementation, the conductive members 120e include a main body 154e, with longitudinal ends in the length direction L and lateral ends in the width direction W, and a crimp region 156e. The conductive wire 152e extends from conductive member to conductive member in an undulating manner and includes regions 162e that extend in the length direction and regions 164e that extend in the width direction. Portions 160e of the conductive wire regions 162e that extend in the length direction are crimped to the conductive members 120e at the crimp regions 156e. In particular, the conductive wire 152e is crimped to each conductive member 120e at only a single location (i.e., crimp region 156e) that is adjacent to only one of the lateral ends of the conductive member. The length of the crimp regions 156e is substantially equal to the length of the conductive members 120e. The regions 162e that extend in the length direction include a portion of the wire 152e with a 180° bend and, accordingly, the regions 164e that extend in the width direction are located adjacent to the same longitudinal ends (i.e., the same ends in the length direction) of the conductive members 120e.

The use of a plurality of spaced, electrically connected conductive members 120e increases the flexibility of the contacts 112e, as compared to otherwise similar contacts that include a single conductive member, thereby increasing the flexibility of the nerve cuff as it moves in and out of its pre-set furled state. The undulating shape of the wire 152e, and associated increase in wire length, further increases the flexibility of the nerve cuff and reduces the likelihood of fatigue failure of the wire, while placement of the regions 164e that extend in the width direction at the same longitudinal end of the conductive members 120e reduces the length of the contacts 112e, thereby facilitating a reduction in length of the nerve cuff.

Figure 26:
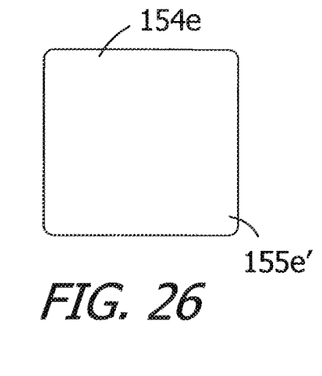
FIG. 26 is a rear view of a portion of the nerve cuff illustrated in FIG. 24 prior to rolling.
Figure 26A:
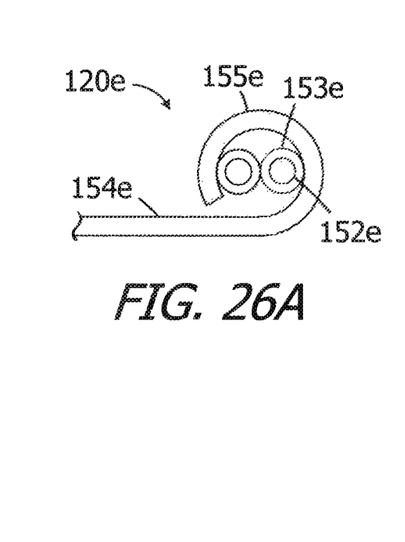
FIG. 26A is a side view of a portion of the nerve cuff illustrated in FIG. 24 prior to being crimped.

With respect to the crimping process, crimp tubes 153e (FIG. 26A) may be provided at spaced locations along the wires 152e and the conductive members 120e may be provided with a rolled portion 155e (FIG. 26A) in which the crimp tubes 153e and associated portions of the wire 152e are located. The conductive members 120d may be provided with a tab 155e' (FIG. 26) that is rolled or folded over the wire 152e and crimp tubes 153e, thereby forming the rolled portions 155e or similar folded portions, prior to crimping and the formation of the crimp regions 156e. The exemplary wires 152e may include a conductor and an insulator, or simply a conductor. In those instances where the wires 152e include a conductor and an insulator, portions of the insulators within the crimp regions may be removed prior to crimping or simply squeeze out of the resulting joint during the crimping process. Other exemplary methods of securing the flexible conductors 152e to conductive members 120e include, but are not limited to, joints that are formed by welding and combined welding/crimping processes.

The contacts 112e and 114 may be individually electrically connected to the plurality contacts 108 on the lead connector 106 (FIG. 2) by wires that extend through the lead body 104 in the manner described above with reference to FIG. 6. In at least some implementations, coiled wires may be employed.

Although the inventions disclosed herein have been described in terms of the preferred embodiments above, numerous modifications and/or additions to the above-described preferred embodiments would be readily apparent to one skilled in the art. It is intended that the scope of the present inventions extend to all such modifications and/or additions. The inventions include any and all combinations of the elements from the various embodiments disclosed in the specification. The scope of the present inventions is limited solely by the claims set forth below.

We claim:

1. An electrode lead, comprising:
an elongate lead body having a proximal end and a distal end; and
a nerve cuff including;
 a biologically compatible, elastic, electrically insulative cuff body affixed to the distal end of the lead body, the cuff body being configured to be circumferentially disposed around a nerve, having a pre-set furled state that defines an inner lumen, being movable to an unfurled state, including front and rear layers, and defining a length, a length direction, a width in the unfurled state that is greater than the length, and a width direction,
 first and second relatively wide electrically conductive members located between the front and rear layers of the cuff body, spaced from one another in the length direction, and extending in the width direction to such an extent that they extend completely around the cuff body inner lumen when the cuff body is in the pre-set furled shape, the cuff body front layer including a plurality of openings that are spaced from one another in the width direction and are aligned with, and located inwardly of the perimeter of, the first relatively wide electrically conductive member and a plurality of openings that are spaced from one another in the width direction and are aligned with, and located inwardly of the perimeter of, the second relatively wide electrically conductive member, a plurality of relatively narrow electrically conductive members located between the front and rear layers of the cuff body, spaced from one another in the width direction, and located between the first and second relatively wide electrically conductive members, the cuff body front layer including a plurality of openings that are spaced from one another in the width direction and are respectively aligned with the relatively narrow electrically conductive members, and a plurality of electrical conductors extending through the lead body from at least some of the electrically conductive members to the proximal end of the lead body.

2. The electrode lead as claimed in claim 1, further comprising:
a plurality of lead connector terminals at the proximal end of the lead body that are connected to the plurality of electrical conductors.

3. The electrode lead as claimed in claim 1, wherein
the first and second relatively wide electrically conductive members are the same length.

4. The electrode lead as claimed in claim 1, wherein
the first and second relatively wide electrically conductive members are parallel to one another.

5. The electrode lead as claimed in claim 1, wherein
all of the relatively narrow electrically conductive members are equidistant from the first and second relatively wide electrically conductive members.

6. The electrode lead as claimed in claim 1, wherein
the relatively narrow electrically conductive members define respective perimeters; and
the plurality of openings that are respectively aligned with the relatively narrow electrically conductive members are located inwardly of the perimeters.

* * * * *